(12) United States Patent
Hamblen et al.

(10) Patent No.: US 6,912,903 B2
(45) Date of Patent: *Jul. 5, 2005

(54) SOIL COMPACTION MEASUREMENT

(75) Inventors: William R. Hamblen, Stow, MA (US); Evan Frank Berkman, Newton Centre, MA (US); Bill G. Watters, late of Essex, MA (US); by Estelle Watters, legal representative, Essex, MA (US)

(73) Assignee: BBNT Solutions LLC, Cambridge, MA (US)

( * ) Notice: Subject to any disclaimer, the term of this patent is extended or adjusted under 35 U.S.C. 154(b) by 48 days.

This patent is subject to a terminal disclaimer.

(21) Appl. No.: 10/461,140

(22) Filed: Jun. 13, 2003

(65) Prior Publication Data

US 2004/0035207 A1 Feb. 26, 2004

Related U.S. Application Data

(63) Continuation-in-part of application No. 09/530,662, filed as application No. PCT/US97/00990 on Jan. 23, 1997, now Pat. No. 6,604,432, which is a continuation-in-part of application No. 08/595,256, filed on Feb. 1, 1996, now abandoned.

(51) Int. Cl.[7] .............................................. G01L 1/00
(52) U.S. Cl. .............................. 73/573; 73/784; 73/594
(58) Field of Search .......................... 73/573, 784, 594, 73/579, 794, 84

(56) References Cited

U.S. PATENT DOCUMENTS

| | | | |
|---|---|---|---|
| 1,871,756 A | 8/1932 | Spath | 73/594 |
| 3,224,253 A | 12/1965 | McKay | 73/594 |
| 3,362,216 A | 1/1968 | Hardin et al. | 73/594 |
| 3,427,877 A | 2/1969 | Swift et al. | 73/146 |
| 3,481,183 A | 12/1969 | Swift | 73/573 |
| 3,643,498 A | 2/1972 | Hardin | 73/594 |
| RE27,875 | 1/1974 | Swift | 73/67.1 |
| 3,795,286 A | 3/1974 | Meyer | 73/594 |
| 3,813,929 A | 6/1974 | Hardin et al. | 73/84 |
| 3,863,202 A | 1/1975 | Landrum, Jr. | 73/594 |
| 3,924,451 A | 12/1975 | Drnevich | 73/67 |
| 3,946,598 A | 3/1976 | Towne et al. | 73/594 |
| 4,127,351 A | 11/1978 | Vural | 404/72 |
| 4,149,253 A | 4/1979 | Paar et al. | 404/84 |
| 4,348,901 A | 9/1982 | Vural et al. | 73/594 |
| 4,382,384 A | 5/1983 | Mitchell et al. | 73/594 |
| 4,445,378 A | 5/1984 | Zuckerwar | 73/594 |
| 4,467,652 A | 8/1984 | Thurner AB et al. | |
| 4,594,899 A | 6/1986 | Henke et al. | 73/784 |

(Continued)

OTHER PUBLICATIONS

"Compaction Monitor", Product Brochure, Gas Research Institute, Foster–Miller, Inc. and Longyear, pp. 1–3 (Jan. 18, 1994).

(Continued)

*Primary Examiner*—Hezron Williams
*Assistant Examiner*—Jacques M. Saint-Surin
(74) *Attorney, Agent, or Firm*—Westman, Champlin & Kelly

(57) ABSTRACT

An apparatus and method are provided for the in-situ measurement of the stiffness of a layer of soil or other surface of interest. The apparatus includes a contact foot for engaging the surface and a drive transducer coupled to the contact foot for applying a vibratory force to the contact foot in response to a drive signal. A motion sensor is coupled to the contact foot and in a preferred embodiment an additional sensor measures the force applied to the contact foot and hence to the surface. These sensors generate corresponding output signals. The output signals are used to generate a measurement signal that is representative of the surface stiffness.

39 Claims, 7 Drawing Sheets

U.S. PATENT DOCUMENTS

| | | | | |
|---|---|---|---|---|
| 4,655,082 | A | | 4/1987 | Peterson .................. 73/594 |
| 4,738,138 | A | | 4/1988 | Redman-White ............ 73/594 |
| 4,750,157 | A | | 6/1988 | Shei ........................ 73/594 |
| 4,912,979 | A | | 4/1990 | Sondergeld et al. ......... 73/594 |
| 4,918,988 | A | | 4/1990 | Ebihara et al. ............. 73/594 |
| 4,995,008 | A | | 2/1991 | Hornbostel et al. .......... 73/594 |
| 5,105,650 | A | | 4/1992 | Atkinson et al. ............ 73/594 |
| 5,398,215 | A | | 3/1995 | Sinha et al. ................ 367/31 |
| 5,996,413 | A | * | 12/1999 | Iyer et al. .................. 73/592 |
| 6,213,681 | B1 | * | 4/2001 | Sick et al. ............. 404/133.05 |
| 6,260,409 | B1 | * | 7/2001 | Briaud et al. ............... 73/86 |
| 6,289,734 | B1 | * | 9/2001 | Daugela .................... 73/573 |
| 6,366,537 | B1 | * | 4/2002 | Sambuelli et al. .......... 367/178 |
| 6,431,790 | B1 | * | 8/2002 | Anderegg et al. ............ 404/75 |
| 6,604,432 | B1 | * | 8/2003 | Hamblen et al. ............ 73/784 |

OTHER PUBLICATIONS

"Field Computer–CCS–RA Compaction Meter", Product Brochure, Dynapac Heavy Equipment AB, pp. 1–4 (Jul. 13, 1993).

"Measurement of the Degree of Compaction by the Impedance Method", T. Tamura and T. Sakai, Journal of Terramechanics, pp. 125–135 (Jan. 1992).

* cited by examiner

US 6,912,903 B2

SOIL COMPACTION MEASUREMENT

CROSS-REFERENCE TO RELATED APPLICATIONS

This application is a continuation-in-part of U.S. application Ser. No. 09/530,662, filed May 2, 2000, now U.S. Pat. No. 6,604,432, which is a Section 371 National Stage Application of International Application No. PCT/US97/00990, filed Jan. 23, 1997 and published as WO97/28432, in English, which is a continuation-in-part of and claims priority from U.S. application Ser. No. 08/595,256, filed Feb. 1, 1996, now abandoned.

FIELD OF THE INVENTION

The present invention relates to the measurement of the properties of soil and more particularly to apparatus for measuring the shear modulus (or other moduli) of soil to determine the extent of compaction.

BACKGROUND OF THE INVENTION

As is understood, soil is an important building material. It serves as the base for virtually all pavements, tunnels and buildings, and thus, can be thought of as an element used in construction. In construction, soil will typically be specified to have certain minimal mechanical properties, e.g., dry density, resilient modulus and strength. While some testing can be conducted in a laboratory, e.g., to determine the suitability of a raw material or blend of materials, it is also typical to perform field tests to assess the soil selection or composition, to determine appropriate site-specific compaction specifications, and to monitor for in-process quality control of the degree of compaction that affects mechanical properties of interest, typically a specified void (as reflected in density) ratio or resilient modulus.

The present field test procedures are typically density measurements made via sand cone or nuclear densitometric methods. A sand cone measurement requires substantial elapsed time while a nuclear densitometric measurement is often not considered sufficiently reliable and also raises radiation concerns. Also, mechanistic design methods require knowledge of or set specifications on soil modulus as a fundamental mechanical property of soil, not density. Accordingly, there exists a need for an ability to do rapid, low cost field tests that will reliably indicate the mechanical properties of the soil. As is understood by those skilled in the art, soil used to fill or level a construction site must be compacted, typically by the application of vibratory energy and weight, in order to obtain the requisite density and modulus. Sometimes, contractors over-compact soil as each of successive layers are added in order to ensure that the result will meet the requisite specification when completed. The ability to quickly and reliably test soil properties could significantly reduce costs due to unnecessary over-compaction and avoid longterm settlement problems due to spatially non-uniform compaction.

While it has previously been proposed to measure soil properties by dynamic impedance measurements, no such prior system has found acceptance since the readings have been found to be inconsistent and not generally repeatable.

SUMMARY OF THE INVENTION

One embodiment of the present invention is directed to an apparatus for the in-situ measurement of the stiffness of a surface. The apparatus includes a spring having an input end, an output end and a spring constant. A contact foot is mechanically coupled to the output end of the spring and has a surface for engaging a region of the surface. A drive transducer is coupled to the input end of the spring for applying a force to the contact foot through the spring. A first motion sensor is coupled to the input end of the spring and generates a first output signal. A second motion sensor is coupled to the output end of the spring and generates a second output signal. A representation of the surface stiffness is derivable from the first and second output signals and the spring constant.

In one embodiment, the spring constant is determined by engineering analysis or by experimental calibration of the device before it leaves the device production facility.

Another embodiment of the present invention is directed to a method of making an in-situ measurement of the stiffness of a surface. The method includes: (a) applying a vibratory force to the surface through a contact foot, which is in contact with the surface; (b) progressively varying a frequency of the vibratory force over a predetermined frequency range; (c) sensing motion of the mechanical foot in response to the vibratory force and generating a corresponding first output signal; and (d) generating a measurement signal, which is representative of the surface stiffness as a function of the first output signal.

Another embodiment of the present invention is directed to an apparatus for the in-situ measurement of the stiffness of a surface. The apparatus includes a weight for providing a static bias force, a contact foot for engaging the surface, and a drive transducer coupled to the foot for applying a vibratory force to the contact foot. The apparatus further includes a resilient connection between the weight and the contact foot, which statically couples the weight to the contact foot and dynamically isolates mass of the weight from motion of the contact foot due to the vibratory force applied to the contact foot.

Another embodiment of the present invention is directed to an apparatus for the in-situ measurement of the stiffness of a surface. The apparatus includes a contact foot for engaging the surface, a drive transducer coupled to the contact foot for applying a vibratory force to the contact foot in response to a drive signal and a waveform generator. The waveform generator generates the drive signal and progressively varies a frequency of the drive signal over a predetermined frequency range. A motion sensor is coupled to the contact foot and generating a corresponding output signal.

BRIEF DESCRIPTION OF THE DRAWINGS

Corresponding reference characters indicate corresponding parts throughout the several views of the drawings.

DETAILED DESCRIPTION OF ILLUSTRATIVE EMBODIMENTS

Figure 1:
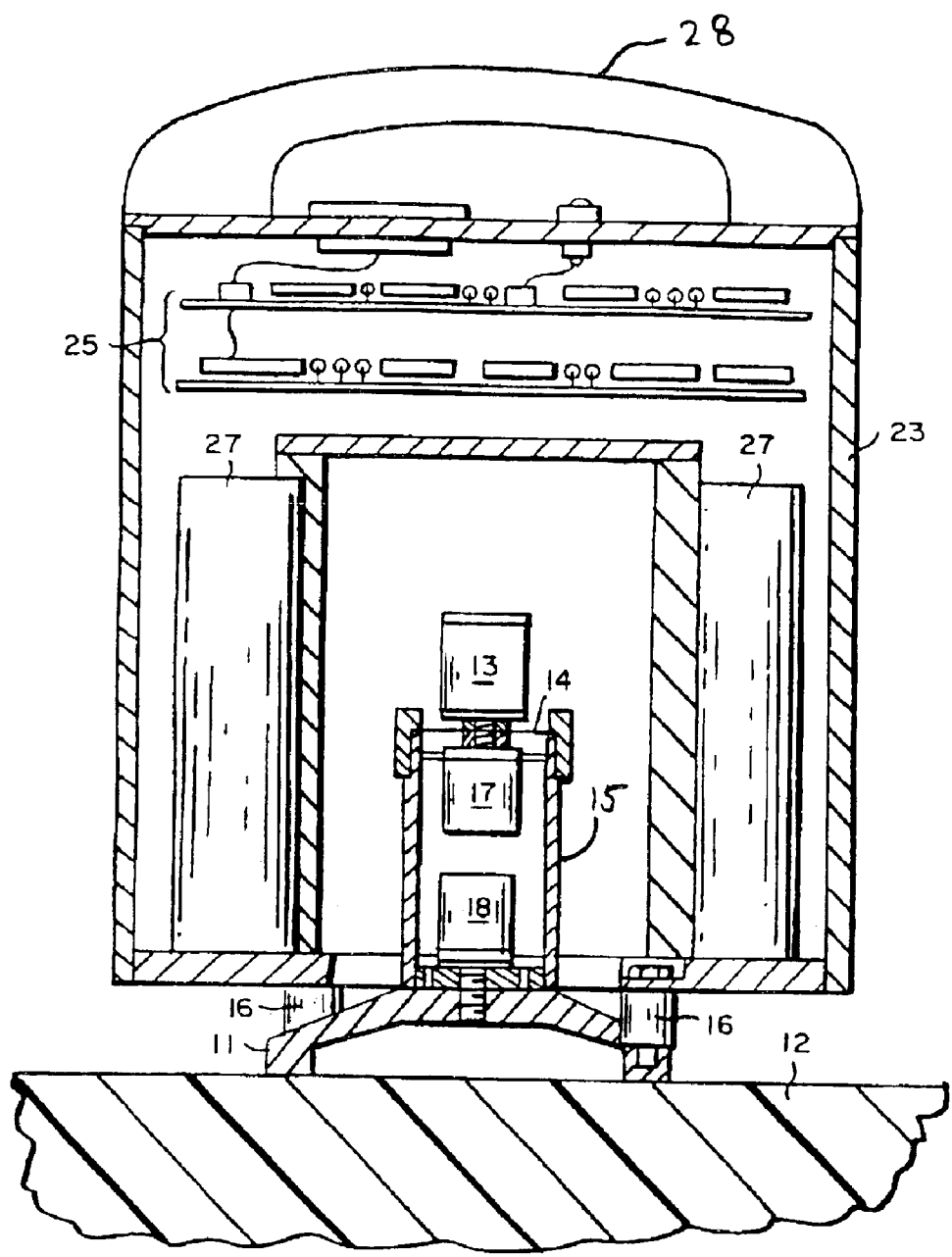
FIG. 1 is a side view of measurement apparatus in accordance with one embodiment of the present invention.

FIG. 1 illustrates an apparatus, which is intended to be man portable so that a worker can easily move it from location to location within a construction site, according to one embodiment of the present invention. The apparatus is designed to stand on a contact foot 11, which, as is described in greater detail hereinafter, engages a defined surface area or region of soil (or other surface, such as asphalt or other pavements) 12 to be tested. The effective depth of measurement of the apparatus is on the order of 1 to 2 times the nominal diameter. In the example embodiment illustrated, the diameter of the foot is about 4½ inches as is appropriate for lifts, or fill layers, up to about 12 inches. Larger or smaller foot diameters may be appropriate in alternate embodiments for measuring soils of different characteristics, providing deeper or limiting effective depth of the measurement, measuring stiffness of other types of surfaces such as pavements, and providing a foot diameter appropriate for other selections of measurement frequency ranges. Likewise, while a circular foot is preferred, it should be understood that a non-circular contact foot member or members might also be used, such as a multiplicity of small circular pads with centers equally-spaced on a larger diameter circle.

A drive transducer, e.g., in the form of an electromechanical linear motor 13, is provided for shaking the contact foot vertically in response to drive signals applied to the transducer. The motor 13 is not connected directly to the foot 11 but rather is connected through a disk-shaped calibrated spring 14 and a cylindrical coupling 15. The output element of motor 13 is connected to the center of the spring 14. When the motor is energized with a dynamic signal, the output element moves the center of the spring, working against the inertial mass of the motor itself. While the spring 14 is circular, it is convenient in terms of force analysis and claim wording to refer to the center of the spring as its input "end" and the periphery of the spring as its output "end", since other forms of calibrated springs could be used.

A first motion sensor (e.g., a velocity sensing geophone) 17 senses the motion at the input end or center of the spring 14 while a second similar sensor (e.g., a geophone) 18 senses the resulting motion of the foot 11, which contacts the soil 12. Since the foot 11 is effectively connected rigidly through cylindrical coupling 15 to the periphery of spring 14, the second motion sensor 18 also provides a measurement of the output end of the spring. Since the stiffness of the spring 14 is predetermined or calibrated and thereby known, the force applied to the foot can be calculated from the difference in the motions (e.g., velocities) measured by the two nominally identical motion sensors 17 and 18.

As is understood by those skilled in the art, the sensors 17 and 18 may include geophones, which are moving coil velocity sensors that provide an output voltage proportional to velocity. The motor 13 can be constituted by a larger geophone with the excitation being applied to the moving coil output element, which is connected to the center of spring 14. However, motion sensors 17 and 18 can measure displacement or acceleration, rather than velocity in alternative embodiments of the present invention.

Housing 23 is mounted on the foot 11 through a set of resilient (that is, compliant) rubber isolation mounts 16. Housing carries an electronics package 25 and batteries 27, which are distributed circumferentially around the axis of the motor 13. Batteries 27 will typically constitute a substantial portion of the weight needed to provide a predetermined downward static bias force on the contact foot 11 due to the force exerted by the mass of batteries 27 under the influence of gravity. The static bias force ensures good contact with the soil and establishes an appropriate static preload stress in the soil under foot 11. If further static bias force is desired, additional inert mass may also be distributed circumferentially around the axis of the device or elsewhere in or on housing 23.

A handle 28 is provided for moving the instrument. In the example embodiment illustrated, the total weight providing a steady downward bias on the foot 11 is about 25 to 35 lbs. As will be understood, the appropriate bias weight will be roughly proportional to the area of soil surface contacted by the foot.

Figure 2:
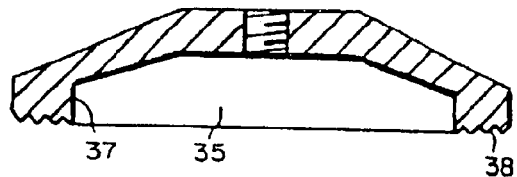
FIG. 2 is a cross-sectional illustration of a contact foot utilized in the apparatus of FIG. 1.

Referring now to FIG. 2, the foot 11 provides a recessed (e.g., arched or domed) central portion 35 and a downwardly projecting annular rim 37 which acts to control the pattern of stress on the soil to the desired distribution. The foot is preferably constructed of a light weight but rigid material, such as aluminum, since the force drop due to accelerating the mass of the foot 11 and other internal structure between the internal reference spring 14 and the ground must be effectively subtracted in order to determine the force applied to the ground and hence the ground impedance as described hereinafter. The thickness of the foot 11 and the elastic modulus of material from which it is made should be sufficiently great that the effective stiffness of the foot 11 is substantially greater (e.g., by a factor of 10 or more) than stiffness of soil or other surface to be measured. If a sufficiently large foot stiffness can not be practically attained, then the compliance of the foot must be corrected for in computing the ground stiffness from the measured stiffness. Also, the bottom surface 38 of the annular rim 37 can be roughened; e.g., by very coarse sand paper, in order to minimize relative horizontal plane motion between the foot and the soil surfaces.

Figure 2A:
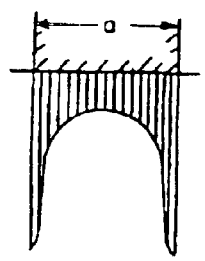
FIGS. 2A–2C are taken from Civil Engineering literature illustrating expected variability in distribution of the pressure on the base of a rigid circular foot. This variability in distribution can lead to variability in the measured stiffness. The annular contact area of the foot of FIG. 2 and of FIG. 4 was chosen to minimize this variability.
Figure 2B:
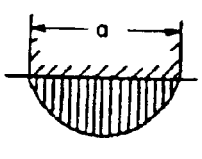
Figure 2C:
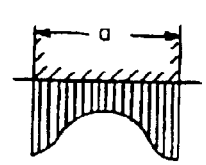

FIGS. 2A, 2B and 2C are taken from Karl Terzaghi and Ralph B. Peck, *Soil Mechanics in Engineering Practice*, John Wiley and Sons, 1967, and represent the distribution of contact pressure on base of smooth rigid footing supported by (a) real, elastic material; b) cohesionless sand; (c) soil having intermediate characteristics. These figures illustrate the motivation for the design of the annular contact area of the foot of FIG. 2. The drastic change in pressure distribution between FIGS. 2A and 2B is believed to be due to slippage between the foot's lower surface and the soil. The annular design of FIG. 2 limits the pressure distribution to an approximation of that in FIG. 2A, a preferred distribution. The rough surface shown on the bottom surface 38 of the annular rim of FIG. 2 is provided to further limit the slippage mechanism.

Figure 3:
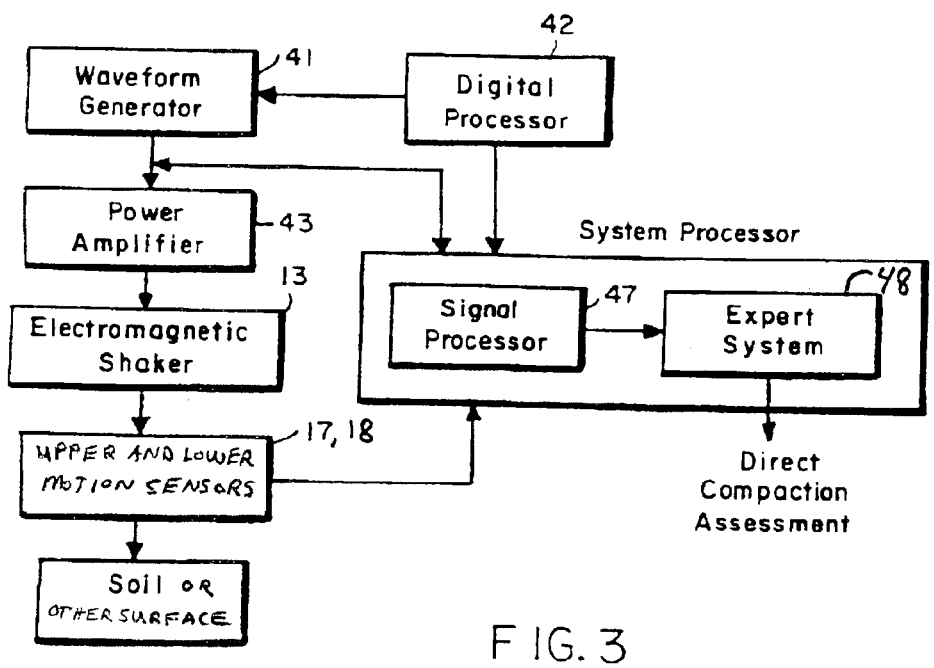
FIG. 3 is a block diagram of drive, sensing and analysis electronics employed in the apparatus of FIG. 1.

Referring now to FIG. 3, the electronic system illustrated there includes a programmable waveform generator 41, according to one embodiment of the present invention. The operation of the waveform generator 41 is initiated and controlled by a programmable digital processor 42. A digital signal processor 47 receives the signals generated by the motion sensors (e.g., geophones) 17 and 18 and also the signal generated by the waveform generator 41. A measure of the displacement of the foot 11 is obtained from motion sensor 18. A measure of the force is obtained from the difference of the two sensor (e.g., geophone) signals and the known spring constant of spring 14. In effect, the desired value of the complex mechanical impedance of the soil (seen through the contact with the foot 11) is obtained by a comparison with the known mechanical impedance of the calibrated spring 14.

If the two motion sensors are geophones (i.e., velocity sensors), then the output of the foot sensor 18 can be integrated to obtain foot displacement, and the difference of the outputs of the two sensors 17 and 18 can be integrated to obtain force (within the proportionality constant of the stiffness of the reference spring 14). However, if measurements are determined as a function of frequency, as in one embodiment, the ratio of the difference in sensor outputs to the foot sensor output can be used directly without integration of the sensors signals (because in the frequency domain, integration is equivalent to a 90° phase shift and division by angular frequency, and these operations are common to both the force and foot sensor outputs from sensors 17 and 18, respectively, which are used only in ratio of one to another).

Under the control of processor 42, the waveform generator 41 generates a swept or stepped sinusoidal signal, for example, which progressively varies in frequency over a pre-selected band; e.g., 50 to 150 Hz or 100 to 200 Hz. Also, the rate of change of frequency can also change so that, for constant amplitude, energy content is greater at some frequencies; e.g., at lower frequencies than at other, higher frequencies. This progression is advantageous in improving signal-to-noise ratio as described in greater detail below. The drive signal provided by the waveform generator 41 is applied through a power amplifier 43 to the motor or drive transducer 13.

As mentioned above, the difference between the outputs of the first and second motion sensors 17 and 18 is proportional to the force that is applied to contact foot 11, while the output of the second motion sensor 18 is proportional to soil displacement. A ratio of these values provides a force-to-displacement ratio.

Both of the force and displacement values (or sensor outputs proportional to force and displacement) have real and imaginary components, where the real component is in-phase and the imaginary component is in-quadrature (90° out of phase) with the drive signal provided by waveform generator 41 (or other reference signal). The real component (and also the imaginary component) of the ratio of force-to-displacement can be derived from the real and imaginary parts of the complex valued force and displacement signals derived from sensors 17 and 18. In one embodiment, the measurement of surface stiffness and the derived measurement of shear modulus are based on only the real part of the force-to-displacement ratio.

It has been found that extracting the real component of the force-to-displacement ratio (i.e., "dynamic stiffness") improves the accuracy of the measurement of the shear modulus, as compared, for example, with using the absolute amplitude of the force-to-displacement ratio, since the imaginary component arises largely due to various energy dissipative mechanisms in the complex behavior of soil. Likewise, while measurement at a single frequency would theoretically be possible, the actual behavior of soil has been found to be somewhat frequency dependent. In addition to potential inherent frequency dependency of soil elastic properties, frequency-dependent behavior or resonances may be caused by (a) standing seismic waves caused by reflections from the sides of a road bed or from the sides of a trench where the soil is being compacted; (b) improper contact between the soil and the measurement foot, and (c) the dynamic interaction between a finite sized foot and an elastic half space. Resonance effects or strong frequency excursions due to nearby boundaries can be minimized or removed by averaging the measured data over a wide frequency range, or else by deleting a narrow band of anomalous data from the average. Thus, the preferred embodiment measures over a range of frequencies to improve signal-to-noise ratio and to minimize the impact of the above listed example anomalies in the stiffness versus frequency response.

In one preferred embodiment, the foot diameter and operational frequency band of the signal provided by the waveform generator 41 are chosen so that the ground input reactance does not differ significantly over the measurement band from its static value (i.e., values at zero frequency).

Given the use of a substantial band of measuring frequencies, the signal-to-noise ratio and the resulting final accuracy can be improved if tracking filters are incorporated into the signal processor. Since measurements are made at one frequency at a time, tracking filters can be used to reject noise in the force and displacement signals at all other frequencies.

One technique for implementing such filters is to use FFT processing, stepping the test frequency from one bin to another bin. Another technique is to utilize synchronous detection, making use of a quadrature (i.e. sine and cosine) oscillator to obtain the desired complex ratio of force to displacement. An advantage of the synchronous detector approach is that much of the signal processing can be done utilizing analog computer techniques, substantially reducing the cost of the analog/digital converter and the digital signal processor.

Another advantage of using a substantial range of frequencies is that interference from tonal noise can be more easily excluded from the final determination, either by operator decision to exclude atypical frequency components, or by an automatic expert system as indicated at reference character 48. An example of a tonal source of interfering noise would be a vibrating soil compactor operating in the general vicinity in which the test measurements are taking place.

Figure 8:
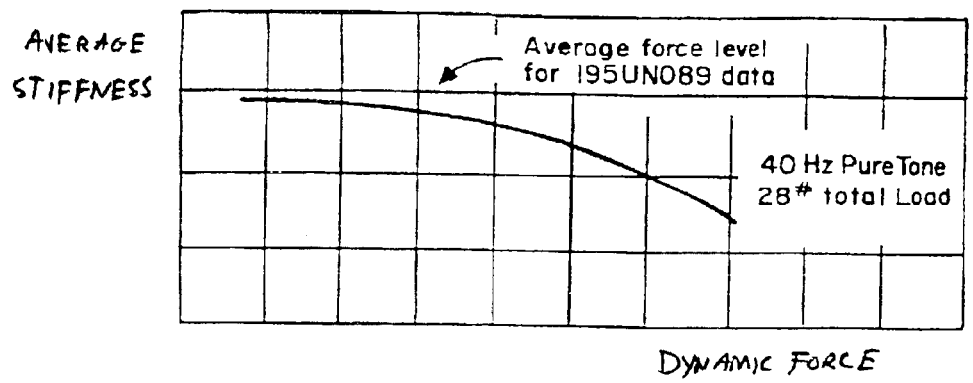
FIG. 8 is a plot of the measured stiffness of compacted soil, showing the measurement error, which can result from using excessively large dynamic force levels.

In order to provide an accurate measurement, the amplitude of the excitation force applied to the shaker motor 13 must be limited to a fairly low level. Otherwise, the measurement process itself can introduce compacting effects or may interfere with the measurement process by causing slippage between adjacent grains of the soil material so that the resultant measurement does not accurately reflect static shear modulus. This effect is illustrated in FIG. 8, where the measured average stiffness of well-compacted "processed gravel" (as might be used as the sub-grade for a highway) is plotted, for a range of dynamic force test levels. Clearly, the poor signal-to-noise ratio, which might exist at a test site where road construction work is in progress cannot be corrected by simply increasing the test force level.

Figure 9:
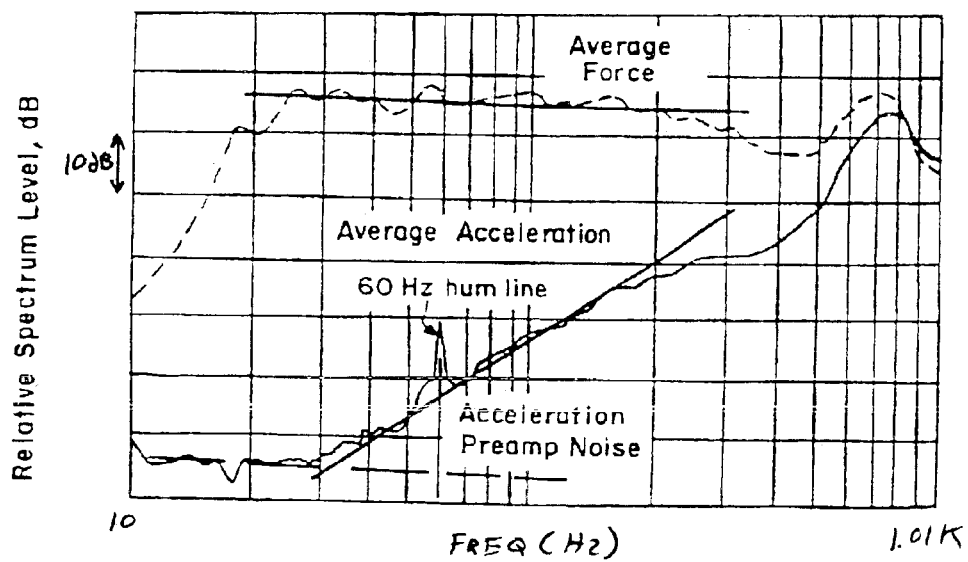
FIG. 9 is a plot of the force spectrum level applied to compacted soil during a field test of its shear modulus, as well as the acceleration spectrum level resulting from the applied force.
Figure 10:
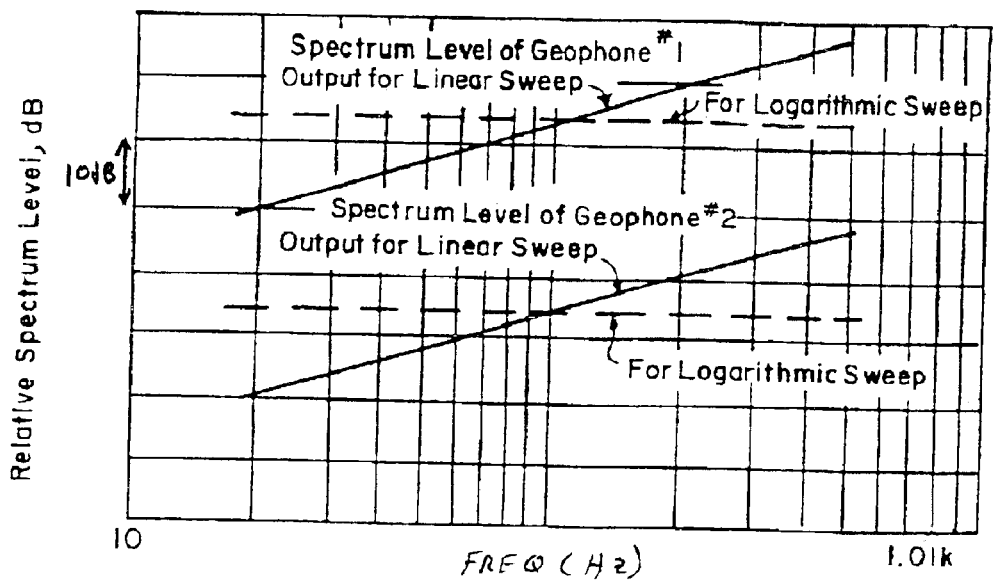
FIG. 10 illustrates the advantage of replacing the accelerometer used for FIG. 9 with a geophone as used in FIG. 1, and the further advantage of using a nonlinear frequency sweep.

FIGS. 9 and 10 illustrate three techniques used in solving the noisy test site problem. FIG. 9 plots measured force and acceleration signal levels on processed gravel at a very quiet test site, using a linear frequency sweep. While the force gauge's signal lies well above its noise floor, the accelerometer's signal is less than the preamp broadband noise at frequencies below about 40 Hz. In addition, a weak hum line at 60 Hz is seen to be about 10 dB above the signal. These measurements were conducted using a commercially available impedance head rather than the instrumentation package illustrated in FIG. 1.

FIG. 10 shows the estimated improvements, first due to substituting a geophone, for the accelerometer used in the commercial impedance head, and then changing the linear sweep to a 20 dB/decade logarithmic sweep, in the 40–400 Hz band (dashed line). That is, the logarithmic frequency sweep spends 10 times as much time in the 40 Hz frequency bin as did the linear sweep; and one-tenth as much time in the 400 Hz bin. In addition, the preamp noise for the low electrical impedance geophone is lower than the preamp noise for the high impedance accelerometer in the commercial head.

While the above two described techniques solve the weak noise problems (e.g., electronic noise), it is clear that much stronger narrow band noise interference (e.g., typical noise due to a rotating weight or oscillating compactor) could be removed by deleting narrow bands from the data. The amount of additional noise reduction provided by a tracking filter will depend on the filter's bandwidth. For example, if the filter is designed to have a constant proportional bandwidth, i.e. a constant Q, then the additional noise reduction should be independent of frequency. For example, a further noise reduction of between 10 and 15 dB is expected for a Q of 10, a significant advantage.

Figure 11:
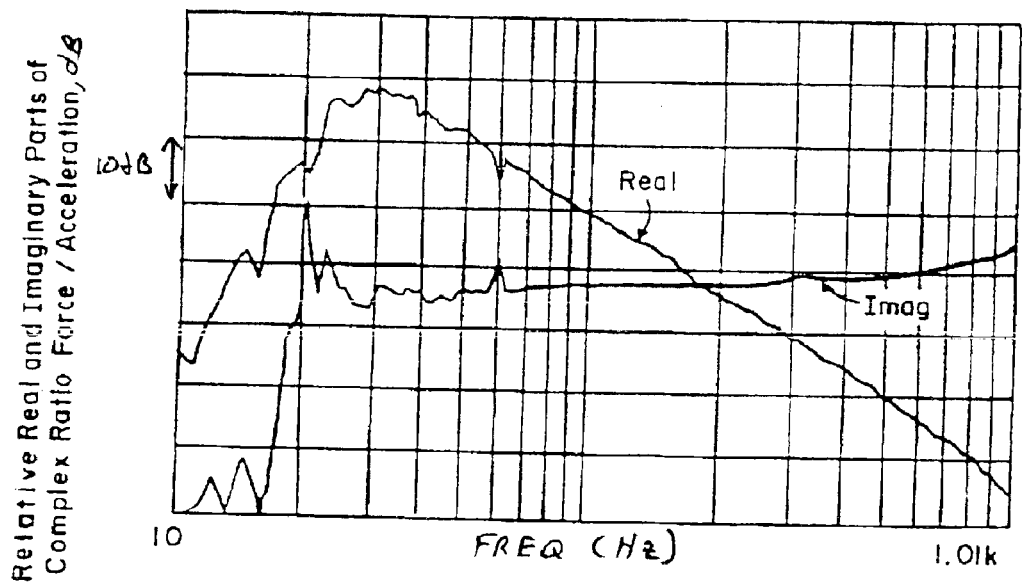
FIG. 11 plots the real and imaginary parts of the complex ratio of the applied force and resulting acceleration signals for FIG. 9.
Figure 12:
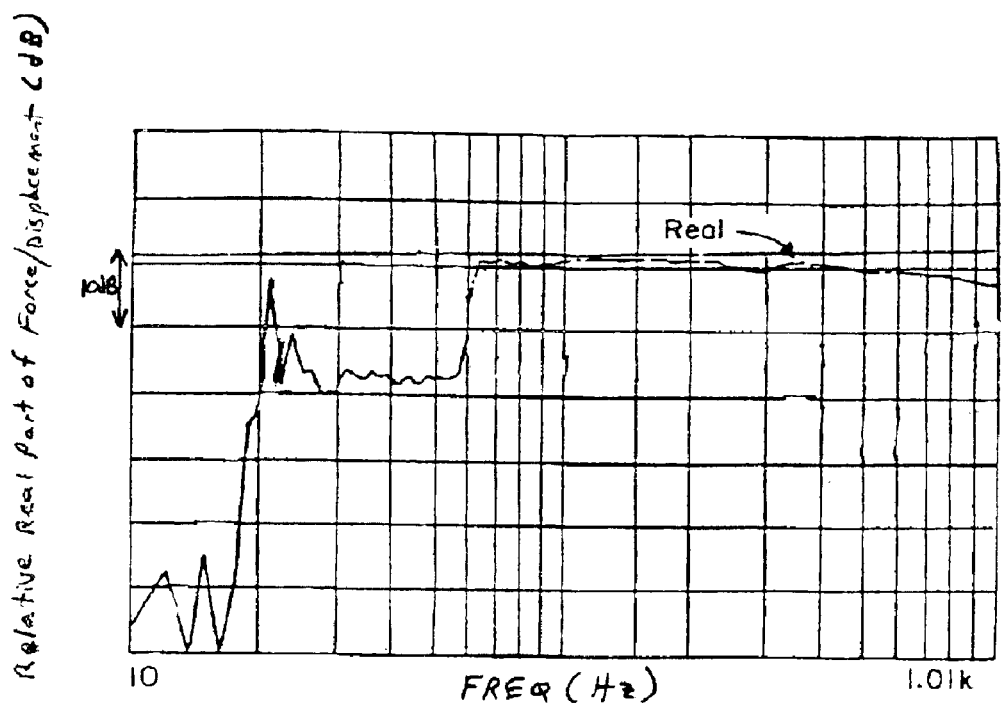
FIG. 12 plots the corresponding real and imaginary parts of the complex ratio of the applied force and the resulting displacement signals.

FIG. 11 plots the complex ratio of force and acceleration, whose power spectra are shown in FIGS. 9 and 10. The plot of the real part (commonly known as a spring line) is seen to be nearly straight. This is shown more clearly in FIG. 12, where the "Real" plot in FIG. 11 has been multiplied by $-\omega^2$ in order to obtain the real part of force-to-displacement. The average of the real part of the stiffness, in the 40 to 400 Hz frequency band is about 90,000 lbs/in.

The analytical relationship between the shear modulus of an ideal half space and the normal mechanical stiffness seen by a rigid circular disk rigidly attached to the surface of the half space is, $$K = \frac{4 \cdot G \cdot a}{(1-\nu)}$$

where:

K is the stiffness (e.g., in lbs/in)

G is the shear modulus (e.g., in lbs/in$^2$, a is the radius of the disk (e.g., in inches)

v is Poisson's Ratio

The result for the rigid annular foot 11 has been found to be very nearly the same as for a rigid circular disk. The soil shear modulus inferred by the above equation for the example 90,000 lbs/in measured stiffness, assuming that $\nu=1/4$, is G=7,600 psi.

The corresponding value of dry density can be estimated from the measured soil stiffness, by using an empirical relationship derived from a large set of field measurements. The mechanical stiffness at each test site was determined using the apparatus of FIG. 1; the dry density was then measured by the sand cone technique. Six different soil types were included in this sampling. The estimated dry density of the soil, which produced FIG. 12 was about 124 lbs/cu ft.

Figure 4:
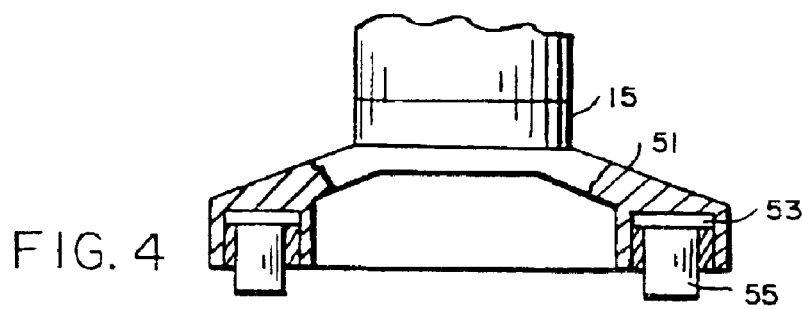
FIG. 4 is a cross-sectional view illustrating an alternate contact foot design.
Figure 5:
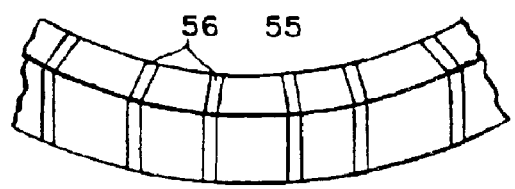
FIG. 5 illustrates a segmented rim employed in the FIG. 4 foot design.

An alternate construction for contacting the soil in the surface area under the contact foot is illustrated in FIGS. 4 and 5. The concept for the annular foot in FIG. 4 is essentially the same as for the annular foot of FIG. 2, except that the articulated design allows the annular foot to conform to a soil surface, which is not flat. In this construction, the foot housing 51 provides an annular groove 53. Fitting into the groove 53 are a series of thin metal segments 55 coupled together by a high glass transition temperature viscoelastic material such as plasticized polyvinyl acetate or a urethane such as PRC's 1564, whose modulus decreases drastically at frequencies below about 100 Hz. Such a material, designated by reference character 56, forms a structure, which is statically soft so as to conform with soil surface irregularity, but is dynamically rigid so as to transmit vibratory energy. An alternate design to achieve the same result over a wide temperature range would make use of a low durometer low glass transition temperature elastomer such as a silicone rubber for element 56, whose modulus would remain low over a wide temperature range, and thus permit the individual segments to slowly conform to the soil surface irregularity. Dynamic rigidity could be achieved by segmenting volume 53 and then filling it with a fluid such as silicone oil. The individual volumes would be coupled together with small orifices.

Figure 6:
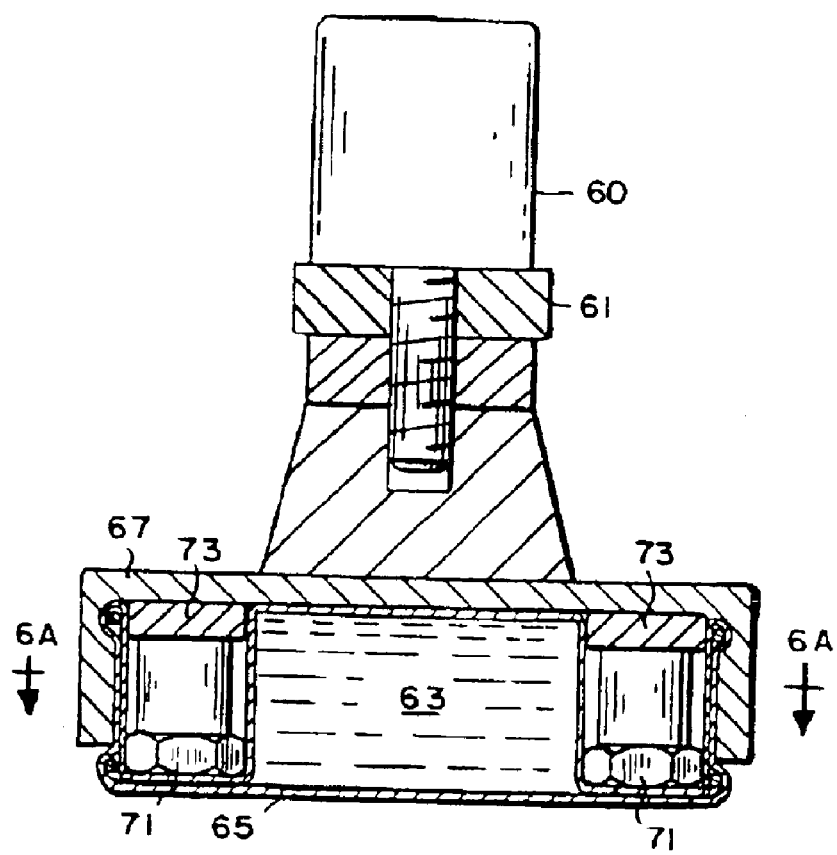
FIG. 6 is a diagram illustrating an alternative construction of contact foot and sensing transducers.
Figure 6A:
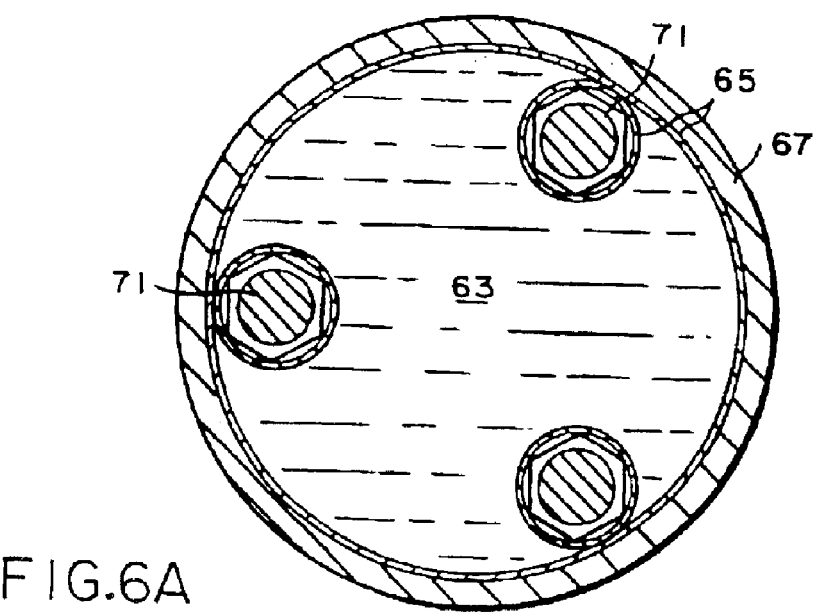
FIG. 6A is a sectional view taken substantially on the line A—A of FIG. 6.

In the embodiment illustrated in FIGS. 6 and 6A, the output of the shaker motor or transducer 60 is coupled to the soil through a force gauge 61 and an oil filled cavity 63 which is defined between top and bottom membranes of a flexible bladder 65 set into a cup-shaped foot 67. The bladder 65 includes a series of pockets, separate from the cavity 63, into which are placed a series of three motion sensors 71. Foam spacers 73 isolate the motion sensors from the vibratory motion of the foot so that they effectively measure only the motion of the soil.

Advantages of this design are the that the lower flexible membrane would apply normal stress to a larger area than would the foot of FIG. 2 or of FIG. 4, and that the membrane should conform to an irregular soil surface much better than would the foot of FIG. 2, and even better than the foot of FIG. 4.

While the bladder is susceptible to puncture, this is dealt with by the fact that three geophones are in contact with the soil's motion without actually being inside the bladder. Likewise, dynamic pressure inside the rubber bag is sensed from outside the bag by the force gauge 61 shown in FIG. 6. Thus, an inadvertent cut in the membrane could quickly be remedied by snapping a spare bladder into place.

Figure 7:
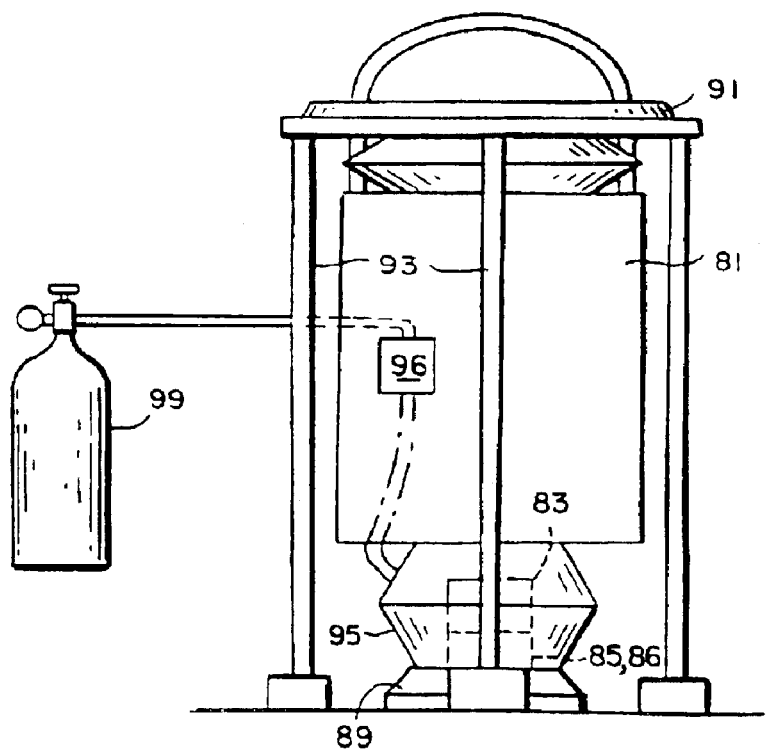
FIG. 7 is a side view of alternate construction of the measurement apparatus providing for automatic variation of bias force.

It is well known that the modulus of soils depends on the effective static stress. The weight of the devices shown in FIG. 1 and FIG. 2 would be chosen to produce a known, typical stress in the soil beneath the foot (reference character 11). To further improve accuracy of measurement, multiple scans of varying frequency excitation may be performed at different levels of downward bias force, i.e. overburden. It is advantageous that the change in bias force be provided automatically. In the embodiment illustrated in FIG. 7, a housing 81 contains the batteries and electronics, separate from the shaker motor 83 and the sensing transducers 85 and 86, which are coupled to the contact foot 89. Coupled to the housing 81 is a frame 91 having a plurality of feet 93, which contact the ground at spaced locations around the contact foot 89. An air spring 95 selectively couples downward force from the housing 81 to the contact foot 89 in accordance with the pressure within the air spring. A tank 99 of compressed air provides a source of air for selectively pressurizing the air spring. Solenoid valves 96, operated under the control of the programmable digital processor incorporated in the electronics package, are provided for selectively venting or filling the air spring. As an alternative, weights could be manually added in a preselected progression to an instrument package such as that illustrated in FIG. 1.

In view of the foregoing it may be noted that the embodiments discussed above provide for the in-situ measurement of soil properties, which allows accurate and repeatable measurements of the stiffness and shear modulus of a surface layer of soil. These measurements can be used as indicators of the state of compaction of the soil. The apparatus can be easily and quickly operated. The apparatus can be easily transported to a construction site and moved between successive measurement positions at the site. The apparatus is highly reliable and is of relatively simple and inexpensive construction.

As various changes could be made in the above constructions and operations without departing from the scope of the invention, it should be understood that all matter contained in the above description or shown in the accompanying drawings shall be interpreted as illustrative and not in a limiting sense. Workers skilled in the art will recognize that changes may be made in form and detail without departing from the spirit and scope of the invention. For example, embodiments of the present invention are not restricted to a man-portable "plant-and-measure" device but are also applicable to devices or systems that may be towed behind a truck or other mobile platform and/or built into compaction equipment for automatic, effectively continuous (or very dense spatial density) measurements. Also, as another example, a calibrated applied force gauge (of various types) and a calibrated foot motion sensor may be used as an alternative to employing two identical motion sensors and a calibrated spring. In this example, the shaker motor applies force to the contact foot directly, without an intervening spring. The calibrated force gauge is attached between the shaker motor and the contact foot to measure the dynamic force applied to the contact foot. The calibrated foot motion sensor measures foot and hence ground motion.

What is claimed is:

1. An apparatus for the in-situ measurement of the stiffness of surface, the apparatus comprising:
   a spring having an input end, an output end and a spring constant;
   a contact foot mechanically coupled to the output end of the spring for engaging a region of the surface;
   a drive transducer coupled to the input end of the spring for applying a force to the contact foot through the spring;
   a first motion sensor coupled to the input end of the spring and generating a first output signal; and
   a second motion sensor coupled to the output end of the spring and generating a second output signal, wherein a representation of the surface stiffness is derivable from the first and second output signals and the spring constant.

2. The apparatus of claim 1 and further comprising a waveform generator, which applies a drive signal to the drive transducer that progressively varies in frequency over a predetermined frequency range.

3. The apparatus of claim 2 wherein the drive signal progressively varies in frequency over the predetermined frequency range at a rate-of-change of frequency that varies with the frequency.

4. The apparatus of claim 1 and further comprising a measurement circuit, which generates a measurement signal that is a function of the stiffness of the surface based on the first and second output signals and the spring constant.

5. The apparatus of claim 4 wherein the measurement circuit generates the measurement signal as a function of a ratio of a difference between the first and second output signals to the second output signal.

6. The apparatus of claim 5 and further comprising a waveform generator, which applies a drive signal to the drive transducer, wherein: a) the difference between first and second output signals, which is proportional to the force, and the second output signal, which is proportional to surface displacement, are both comprised of real and imaginary components, where the real component is in-phase and the imaginary component is in-quadrature with the drive signal and b) the measurement signal is based on only a real component of the ratio.

7. The apparatus of claim 1 wherein the contact foot comprises a downwardly extending annular rim for contacting the surface and a recessed central region.

8. The apparatus of claim 1 wherein the contact foot comprises a plurality of rigid segments joined by a less rigid material.

9. The apparatus of claim 1 wherein the contact foot comprises a plurality of contact feet members for engaging the surface.

10. The apparatus of claim 1 and further comprising:
    a weight for providing a static bias force to the contact foot; and
    a resilient connection between the weight and the contact foot, which statically couples the static bias force to the contact foot and dynamically isolates a mass of the weight from motion of the contact foot due to the force from the drive transducer.

11. The apparatus of claim 10 wherein the resilient connection comprises a rubber isolation mount, through which the contact foot is mounted to the weight.

12. The apparatus of claim 10 and further comprising a housing having an internal cavity, wherein:
    the housing carries the weight circumferentially around the internal cavity;
    the drive transducer is supported within the internal cavity by the contact foot; and
    the contact foot is mounted to the housing through the resilient connection.

13. A method of making an in-situ measurement of the stiffness of a surface, the method comprising:
    (a) applying a vibratory force to the surface through a contact foot, which is in contact with the surface;
    (b) progressively varying a frequency of the vibratory force over a predetermined frequency range;
    (c) sensing motion of the mechanical foot in response to the vibratory force and generating a corresponding first output signal; and (d) generating a measurement signal, which is representative of the surface stiffness as a function of the first output signal.

14. The method of claim 13 wherein (b) comprises progressively varying the frequency of the vibratory force over the predetermined frequency range at a rate-of-change of frequency that varies with the frequency.

15. The method of claim 13 wherein (d) comprises generating the measurement signal at a plurality of the frequencies in the predetermined frequency range to produce a plurality of measurement samples and averaging the measurement samples to produce an average.

16. The method of claim 15 wherein (d) comprises removing anomalous data by removing from the average the measurement sample produced within at least one of the plurality of frequencies.

17. The method of claim 13 wherein:
step (a) comprises coupling a drive transducer to an input end of a calibrated spring, coupling the contact foot to an output end of the calibrated spring and generating the vibratory force with the drive transducer;
step (c) further comprises sensing the vibratory force at the input end of the calibrated spring and generating a corresponding second output signal; and
step (d) comprises generating the measurement signal as a function of the first and second output signals.

18. The method of claim 17 wherein (d) further comprises generating the measurement signal as a function of a ratio of a difference between the first and second output signals to the first output signal.

19. The method of claim 18 wherein the first and second output signals comprise real and imaginary components, where the real component is in-phase and the imaginary component is in-quadrature with the vibratory force and the measurement signal is generated in step (d) based on only a real component of the ratio.

20. The method of claim 13 and further comprising:
step (a) comprises coupling a drive transducer directly to the contact foot and generating the vibratory force with the drive transducer;
step (c) further comprises sensing the vibratory force generated by the drive transducer and generating a corresponding second output signal; and
step (d) comprises generating the measurement signal as a function of the first and second output signals.

21. The method of claim 13 wherein (a) comprises:
supplying a static bias force from a weight;
statically coupling the static bias force to the contact foot through a resilient connection between the weight and the contact foot; and
dynamically isolating mass of the weight from motion of the contact foot through the resilient connection.

22. The method of claim 20 wherein (a) further comprises:
supporting the weight with a housing having an internal cavity;
supporting a drive transducer within the internal cavity by the contact foot;
generating the vibratory force with the drive transducer; and
mounting the contact foot to the housing through the resilient connection.

23. An apparatus for the in-situ measurement of the stiffness of a surface, the apparatus comprising:
a weight for providing a static bias force;
a contact foot for engaging the surface;
a drive transducer coupled to the foot for applying a vibratory force to the contact foot; and
a resilient connection between the weight and the contact foot, which statically couples the weight to the contact foot and dynamically isolates mass of the weight from motion of the contact foot due to the vibratory force applied to the contact foot.

24. The apparatus of claim 23 wherein the resilient connection comprises a rubber isolation mount, through which the contact foot is mounted to the weight.

25. The apparatus of claim 23 and further comprising:
a housing having an internal cavity, wherein the housing carries the weight circumferentially around the internal cavity, the drive transducer is supported within the internal cavity by the contact foot, and the contact foot is mounted to the housing through the resilient connection.

26. The apparatus of claim 23 wherein the contact foot comprises a downwardly extending annular rim for contacting the surface and a recessed central region.

27. The apparatus of claim 23 wherein the contact foot comprises a plurality of rigid segments joined by a less rigid material.

28. The apparatus of claim 23 wherein the contact foot comprises a plurality of contact feet members for engaging the surface.

29. The apparatus of claim 23 and further comprising:
a spring having an input end, an output end and a spring constant, wherein the drive transducer is coupled to the input end of the spring;
a first motion sensor coupled to the input end of the spring and generating a first output signal; and
a second motion sensor coupled to the output end of the spring and generating a second output signal, wherein a representation of the surface stiffness is derivable from the first and second output signals and the spring constant.

30. The apparatus of claim 29 and further comprising a measurement circuit, which generates a measurement signal that is a function of the stiffness of the surface based on the first and second output signals and the spring constant.

31. The apparatus of claim 30 wherein the measurement circuit generates the measurement signal as a function of a ratio of a difference between the first and second output signals to the second output signal.

32. The apparatus of claim 31 wherein the first and second output signals comprise real and imaginary components, where the real component is in-phase and the imaginary component is in-quadrature with the vibratory force and the measurement signal is generated in step (d) based on only a real component of the ratio.

33. The apparatus of claim 23 and further comprising:
a force gauge, which is coupled between coupled between the drive transducer and the contact foot to measure the vibratory force applied to the contact foot and which generates a first output signal; and
a motion sensor, which is coupled to the contact foot to measure motion of the contact foot and which generates a second output signal, wherein a representation of the surface stiffness is derivable from the first and second output signals.

34. The apparatus of claim 23 and further comprising a waveform generator, which applies a drive signal to the drive transducer that progressively varies in frequency over a predetermined frequency range.

35. The apparatus of claim 34 wherein the drive signal progressively varies in frequency over the predetermined frequency range at a rate-of-change of frequency that varies with the frequency.

36. An apparatus for the in-situ measurement of the stiffness of a surface, the apparatus comprising:
 a contact foot for engaging the surface;
 a drive transducer coupled to the contact foot for applying a vibratory force to the contact foot in response to a drive signal;
 a waveform generator, which generates the drive signal and progressively varies a frequency of the drive signal over a predetermined frequency range; and
 a first motion sensor coupled to the contact foot and generating a corresponding first output signal.

37. The apparatus of claim 36 wherein the waveform generator progressively varies the frequency of the vibratory force over the predetermined frequency range at a rate-of-change of frequency that varies with the frequency.

38. The apparatus of claim 36 and further comprising:
 a spring having an input end and an output end, wherein the drive transducer is coupled to the input end and the contact foot is coupled to the output end;
 a drive transducer coupled to the input end of the spring for applying a force to the contact foot through the spring; and
 a second motion sensor coupled to the input end of the spring and generating a second output signal, wherein a representation of the surface stiffness is derivable from the first and second output signals.

39. The apparatus of claim 36 and further comprising:
 a force gauge, which is coupled between coupled between the drive transducer and the contact foot to measure the vibratory force applied to the contact foot and which generates a second output signal, wherein a representation of the surface stiffness is derivable from the first and second output signals.

* * * * *